US005296159A

United States Patent [19]

Wilson et al.

[11] Patent Number: 5,296,159

[45] Date of Patent: Mar. 22, 1994

[54] MILD SOAP-SYNBAR

[75] Inventors: David B. Wilson; Charles D. Tereck; Donald A. Niederbaumer; Robert G. Bartolo; Francisco A. Pichardo, all of Cincinnati; TImothy J. Welch, West Chester, all of Ohio

[73] Assignee: The Procter & Gamble Company, Cincinnati, Ohio

[21] Appl. No.: 988,323

[22] Filed: Dec. 16, 1992

Related U.S. Application Data

[63] Continuation-in-part of Ser. No. 844,012, Feb. 28, 1992, abandoned.

[51] Int. Cl.⁵ ....................... C11D 9/30; C11D 17/00; C11D 10/04

[52] U.S. Cl. .................................... 252/117; 252/134; 252/DIG. 5; 252/DIG. 16; 252/174.21

[58] Field of Search ................ 252/117, 134, DIG. 5, 252/DIG. 16, 174.21

[56] References Cited

U.S. PATENT DOCUMENTS

| | | | |
|---|---|---|---|
| 4,540,507 | 9/1985 | Grollier | 252/174 |
| 4,673,525 | 6/1987 | Small et al. | 252/132 |
| 4,704,224 | 11/1987 | Sand | 252/132 |
| 4,812,253 | 3/1989 | Small et al. | 252/132 |
| 4,820,447 | 4/1989 | Medcalf, Jr. et al. | 252/117 |
| 4,874,528 | 10/1989 | Dawson et al. | 252/117 |
| 4,946,618 | 8/1990 | Knouchel et al. | 252/117 |
| 4,985,170 | 1/1991 | Dawson et al. | 252/117 |
| 5,064,555 | 11/1991 | Medcalt, Jr. et al. | 252/118 |
| 5,076,953 | 12/1991 | Jordan et al. | 252/108 |
| 5,096,608 | 3/1992 | Small et al. | 252/132 |

*Primary Examiner*—Paul Lieberman
*Assistant Examiner*—Michael P. Tierney
*Attorney, Agent, or Firm*—Betty J. Zea; Robert B. Aylor; Steven J. Goldstein

[57] ABSTRACT

Mild soap bars containing low levels of cationic polymeric skin mildness aid, polyethoxylated nonionic detergent surfactant to decrease scum formation and inhibit frosting, i.e., crystallization of nonionic detergent surfactant on the bar surface, and water. These bars are not beta-phase bars.

16 Claims, No Drawings

BEST AVAILABLE COPY

MILD SOAP-SYNBAR

CROSS-REFERENCE TO RELATED APPLICATION

This is a continuation-in-part application of U.S. Ser. No. 07/844,012, filed Feb. 28, 1992, now abandoned.

TECHNICAL FIELD

This invention relates to cleansing soap bars, preferably superfatted, containing cationic polymer mildness additive and a nonionic surfactant for scum dispersion.

BACKGROUND OF THE INVENTION

The formulation of ultra-mild personal cleansing preparations has become a focus of great interest. When people wash and scrub their skin with various surface-active preparations frequently, mildness is very important. Ideal cleansers should be cost effective, cleanse gently and rinse well. Most toilet bars fall short in this respect.

Synthetic detergents are relatively expensive. None of the synthetic products as yet matches the low cost of soap when compared on a 100% active ingredient basis.

The use of synthetic detergent surfactants in soap bars is well known, being documented in U.S. Pat. Nos.: 2,988,511, Mills et al., issued Jun. 13, 1961; 3,043,778, Kelly, issued Jul. 10, 1962; and 3,598,746, Kaniecki et al., issued Aug. 10, 1971, said patents being incorporated herein by reference.

U.S. Pat. No. 4,180,470, Tokosh et al., issued Dec. 25, 1979, incorporated herein by reference, discloses a method for making improved acyl isethionate detergent bars with from 2-6% of sodium alkoxy hydroxy propane sulfonate (a synonym for alkyl glyceryl ether sulfonate) with alkyl chains of from 8 to 22 carbon atoms in conjunction with a small amount of sodium chloride.

Commonly assigned U.S. Pat. No. 4,820,447, Medcalf et al., issued April, 1989, incorporated herein by reference, discloses a mild soap bar comprising a polymeric skin mildness aid. Commonly assigned U.S. Pat. No. 4,985,170, Dawson et al., entitled "In Beta-Phase Bar Form Containing Soap, High HLB Nonionic Surfactant, and Water-Soluble Polymer," issued Jan. 15, 1991, and U.S. Pat. Nos.: 2,988,511, supra; 2,989,547, Whyte, issued Jun. 20, 1961; 2,999,068, Pilcher et al., issued Sep. 5, 1961; and 3,024,273, Whyte et al., issued Mar. 6, 1962, are all incorporated herein by reference.

SUMMARY OF THE INVENTION

This invention is an improved milled, mild personal cleansing soap-synthetic bar comprising: a mixture of soap, a cationic polymeric skin mildness aid, a selected $C_{14}$-$C_{20}$ alkyl polyethoxylate (65-100) nonionic detergent surfactant for inhibiting frosting and the formation of crystals on the bar surface upon storage, and water. The selected nonionic also inhibits scum formation. The bars of this invention have good lather characteristics.

DETAILED DESCRIPTION OF THE INVENTION

Disclosed is a milled soap-synthetic bar comprising: (1) from about 45% to about 90%, preferably from about 55% to about 80%, more preferably from about 70% to about 80% soap; (2) from about 0.5% to about 5%, preferably from about 0.5% to about 2% of cationic polymeric skin mildness aid; (3) from about 1% to about 8%, preferably from about 2% to about 5% of $C_{14}$-$C_{20}$, preferably $C_{16}$-$C_{18}$, fatty alkyl (alcohol) polyethoxylate (from about 65 to about 100, preferably from about 70 to about 90, more preferably about 80 moles of ethylene oxide moieties per molecule) nonionic detergent surfactant; and (4) from about 7% to about 12%, preferably from about 8% to about 10% water. The ratio of the nonionic detergent surfactant to soap is from about 1:90 to about 1:5, preferably from about 1:40 to about 1:10. The bar of the present invention is not a beta-phase bar.

The terms "soap-synthetic bar," also "soap-synbar," as used herein mean that the bar has more soap than synthetic surfactant unless otherwise specified.

The percentages, ratios, and parts herein are on a weight basis, unless otherwise specified. All levels and ranges herein are approximations unless otherwise specified.

It is noted that surfactant mildness can be measured by a skin barrier destruction test which is used to assess the irritancy potential of surfactants. In this test the milder the surfactant, the less of the skin barrier is destroyed. Skin barrier destruction is measured by the relative amount of radiolabeled water ($^3H$-$H_2O$) which passes from the test solution through the skin epidermis into the physiological buffer contained in the diffusate chamber. This test is described by T. J. Franz in the J. Invest. Dermatol., 1975, 64, pp. 190-195; and in U.S. Pat. No. 4,673,525, Small et al., issued Jun. 16, 1987, incorporated herein by reference. Barrier destruction testing shows that the bars of this application are mild.

(1) Soap

The soap bar of this invention comprises from about 45% to about 90% soap, preferably at least 25% of which is tallow soap. The abbreviation "CN" means "coconut," "POS" means "palm oil stearin," and "T" means tallow herein, unless otherwise specified. A preferred bar of this invention comprises about 1.5/1 T/CN fatty acid soap mixture. Another preferred bar of this invention comprises about 0.75/0.75/1 T/POS/CN fatty acid soap mixture. The fatty acid soaps which are essentials of this invention are alkali metal soaps of fatty acids having alkyl chain lengths Of $C_8$-$C_{22}$, preferably $C_{12}$-$C_{18}$, and especially those of the $C_{10}$-$C_{14}$ chain lengths which are important in producing lather rapidly and of good, highly acceptable quality. The alkali metal is typically sodium, or a mixture of sodium and potassium. It is understood that coconut soap is interchangeable with palm kernel oil soap. The fatty acid soaps are preferably present at a level of about 55-90%, and most preferably about 70-80%. A preferred soap has a ratio of tallow/coconut soap of from about 1:1 to about 9:1, preferably from about 1:1 to about 1.5:1. Another preferred soap has a ratio of tallow/palm oil stearin/-coconut soap of from about 0.5:0.5:1 to about 4.5:4.5:1, preferably from about 0.70:0.70:1 to about 1:1:1.

(2) Cationic Polymeric Skin Mildness Aid

Bars of this invention also comprise from about 0.5% to about 5%, more preferably from about 0.5% to about 2%, cationic polymer, preferably suitably fast hydrating polymer that acts to improve skin mildness. As used herein the term "cationic polymer" includes naturally and synthetically derived cationic polymers. The polymers have molecular weights of from about 1,000 to about 3,000,000. A preferred one is selected from cationic guar gums having a molecular weight range of 2,500–350,000.

U.S. Pat. Nos.: 4,820,447, Medcalf et al., supra; 4,985,170, Dawson and Ridley, issued Jan. 15, 1991; and 4,946,618, Knochel et al., issued Aug. 7, 1990, all of said patents being incorporated herein by reference, disclose polymeric skin mildness aids of the type useful herein.

Bar soap compositions containing relatively small amounts of these cationic polymeric skin mildness aids deliver significantly improved clinical mildness relative to compositions without such polymers. The resultant mildness approaches that of syntheticbased skin cleansing products. (It is known that certain synbars are generally milder than those based on soap, particularly the lower chain length fatty acid soaps.) The mildness improvement is further demonstrated by an improved barrier function of the stratum corneum relative to a product without polymer, as determined by measurement of transepidermal water loss. The cationic polymers used in this invention also provide a desirable silky, soft, smooth in-use feeling. It is believed that the positively charged polymer combines with the negatively charged sites on the skin to provide a soft skin feel after use.

Suitable cationic polymer (skin conditioning agent) can be selected from the group consisting of:

(I) cationic polysaccharides;

(II) cationic copolymers of saccharides and synthetic cationic monomers, and (III) synthetic polymers selected from the group consisting of:

(A) cationic polyalkylene imines (B) cationic ethoxy polyalkylene imines, and (C) cationic poly[N-[-3-(dimethylammonio)propyl]-N'-[3-(ethyleneoxyethylene dimethylammonio)-propyl]urea dichloride].

Specific examples of members of the cationic polysaccharide class include the cationic hydroxyethyl cellulose JR 400 made by Union Carbide Corporation; the cationic starches Stalok® 100, 200, 300 and 400 made by Staley, Inc.; the cationic galactomannans based on guar gum of the Galactasol 800 series by Henkel, Inc., and the Jaguar Series by Rhône-Poulenc Corporation.

Examples of members of the class of copolymers of saccharides and synthetic cationic monomers include those composed of cellulose derivatives (e.g., hydroxyethyl cellulose) and N,N-diallyl,N-N-dialkyl ammonium chloride available from National Starch Corporation under the trade name Celquat.

Some cationic synthetic polymers useful in the present invention are cationic polyalkylene imines, ethoxypolyalkylene imines, and poly[N-[-3-(dimethylammonio)propyl]-N'-[3-(ethyleneoxyethylene dimethylammonio)propyl]urea dichloride]the latter of which is available from Miranol Chemical Company, Inc., under the trademark of Miranol A-15, CAS Reg. No. 68555-36-2.

Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anhydroglucose unit to about 0.80 per anhydroglucose unit with the substituent cationic group being the adduct of 2,3-epoxypropyltrimethyl ammonium chloride to the natural polysaccharide backbone. Examples are JAGUAR C-14-S, C-15, C-17, and C-376FA sold by Rhône-Poulenc Corporation. In order to achieve maximum mildness benefits, the polymer should have characteristics, either structural or physical, which allow it to be suitably and fully hydrated and subsequently well incorporated into the soap matrix.

(3) Nonionic Detergent Surfactant

The compositions herein also contain an ethoxylated nonionic surfactant. The nonionic surfactant is valuable for improving formulation characteristics in the area of scum formation under hard water usage conditions. The ethoxylated nonionic surfactant and polymer can be incorporated in the compositions of the invention without detriment to the bar. Preferred from the viewpoint of scum dispersion are ethoxylated nonionic surfactants having a hydrophilic balance (HLB) of from about 10 to about 19.5, preferably from about 15 to about 19.2, more preferably from about 17 to about 19, HLB being defined in the usual manner as W/5, where W is the weight percent of ethylene oxide per mole of surfactant. The level of nonionic detergent surfactant is preferably from about 1% to about 8%, more preferably from about 2% to about 5%.

Preferred ethoxylated nonionic surfactants for use herein have a melting point in the range of from about 32° C. to about 90° C., preferably from about 35° C. to about 70° C. The melting point is taken herein to refer to the temperature at which the melting is completed and is conveniently measured by thermal analysis using a Dupont 910 Differential Scanning Calorimeter with Mechanical Cooling Accessory and R90 Thermal Analyser as described for example in EP-A-0142910.

Preferred nonionic surfactants herein are the condensation products of primary and secondary fatty alcohols having from about 14 to about 22, preferably from about 16 to about 18, atoms in either, preferably, straight or branched chain configuration, with from about 65 to about 100, preferably from about 70 to about 90, more preferably about 80 moles of ethylene oxide per mole of alcohol. Examples of surfactants of this type are the condensation products of hardened tallow alcohol with an average of between 65 and 100 moles, preferably about 80 moles of ethylene oxide per mole of alcohol, the tallow portion comprising essentially between 16 and 18 carbon atoms and preferably having a straight chain hydrophobic group with only minimal, preferably no branching.

(4) Water

The bars of the present invention contain from about 7% to about 12%, preferably from about 8% to about 10% water. The bars of this invention are not beta-phase bars. Beta-phase soap bars usually contain at least 15% water. See U.S. Pat. Nos.: 4,719,030, Williams et al., issued Jan. 12, 1988; and 4,985,170, supra, both incorporated herein by reference.

Acyl Isethionate Detergent Surfactant

Commonly assigned U.S. Pat. Application Ser. No. 07/744,148, Wilson et al., filed Aug. 13, 1991, discloses an improved milled, mild personal cleansing bar comprising: a mixture of soap, a cationic polymeric skin mildness aid, and a mixture of a $C_{14}$–$C_{20}$ alkyl polyethoxylate (20–250) nonionic detergent surfactant and a $C_{10}$–$C_{18}$ acyl isethionate detergent surfactant for inhibiting scum formation and maintaining good lather characteristics. Optionally, acyl isethionate detergent surfactants can be used in the present invention. They contain acyl chains having from about 10 to about 18, preferably from about 12 to about 16, carbon atoms. Acyl groups derived from coconut are desirable. The cation is typically sodium or a mixture of sodium and potassium and can be the same as for the soap.

The nonionic detergent surfactant tends to lower the sudsing (lather) of the bar. Addition of the acyl isethionate detergent surfactant improves the lather and aids in mildness and processing. The level of acyl isethionate detergent surfactant is typically from about 0.5% to about 10%, preferably from about 1% to about 8%, more preferably from about 2% to about 5%. However, in the present invention, selected soaps can be used to provide good lather without acyl isethionate.

Moisturizing

Preferred bars also contains from about 2% to about 15%, preferably from about 7% to about 12%, moisturizer, preferably one selected from glycerin and, more preferably, free fatty acid, or mixtures thereof. An even more preferred bar of this invention contains at least about 9% moisturizer. The fatty acid is present typically from about 4% to about 8%, preferably from about 4.5%,,to about 7%, and the glycerin is typically present at from about,, 2% to about 6%, preferably from about 3% to about 5%.

Miscellaneous Minor Ingredients

Other useful ingredients include long chain alkyl sulfates.

Long chain alkyl sulfates are excellent additions to soap/synbar compositions. The long chain alkyl sulfates provide an improvement in bar processability, while not significantly impairing bar mildness or the desirable physical characteristics of the bars.

Such long chain, e.g., $C_{16}$–$C_{18}$ alkyl sulfates are derived from corresponding saturated straight chain alcohols. The $C_{16}$–$C_{18}$ alkyl sulfates preferably comprise said C16–$C_{18}$ alkyl chains at a level of at least about 90%, preferably about 93%, and more preferably about 97%. In general , the ratio Of $C_{16}$ to $C_{18}$ can range from about 4:1 to about 1:4 by weight. A commercially available $C_{16}$–$C_{18}$ alkyl sulfate is SIPON® EC-111 (formerly SIPEXO EC-111), sodium cetearyl sulfate, which is approximately 60% C16 and 36% Cl8- SIPON® EC-111 is sold by Alcolac Company, Baltimore, MD 21226. Another source is Henkel Corp., Ambler, PA 19002. Henkel's sodium cetearyl sulfate, LANETTE E, is an estimated 50–50% $C_{16}$–$C_{18}$ alkyl sulfate sold as an emulsifier.

The long chain alkyl sulfate can comprise 0–30% by weight of the bars of this invention.

Other soap bar ingredients can be selected from: other surfactants, other polymeric skin feel aids, fillers, etc.

Limited amounts of other detergent surfactants can be used; particularly from about 0.1% to about 5%, preferably from about 0.2% to about 1%, of other lather enhancing detergent co-surfactants, e.g., mild ones, e.g., sodium lauroyl sarcosinate. Numerous examples of other mild surfactants are disclosed in the patents incorporated herein by reference. They include limited amounts of other anionic acyl sarcosinates, methyl acyl taurates, N-acyl glutamates, alkyl sulfosuccinates, alkyl phosphate esters, ethoxylated alkyl phosphate esters, protein condensates, ethoxylated alkyl sulfates, alkyl amine oxides, betaines, sultaines, and mixtures thereof. Included in the ethoxylated alkyl sulfate detergent surfactants are the alkyl ether sulfates with 0.5 to 10 ethoxy groups, especially ammonium and sodium lauryl ether sulfates. Alkyl chains for these other mild surfactants are $C_8$–$C_{22}$, preferably $C_{10}$–$C_{18}$. Alkyl glycosides and methyl glucose esters are preferred mild nonionics which can be mixed with other mild anionic or amphoteric surfactants in the compositions of this invention.

Other minor ingredients of the present invention can be present. E.g., perfumes can be used in formulating the skin cleansing products, generally at a level of from about 0.1% to about 1.5% of the composition. Alcohols, hydrotropes, colorants, and fillers such as talc and cl ay, can al so be used. Cetearyl alcohol is a mixture of cetyl and stearyl alcohols. Preservatives, e.g., sodium ethylenediaminetetraacetate (EDTA), generally at a level of less than 1% of the composition, can be incorporated in the cleansing products to prevent color and odor degradation. Antibacterials can also be incorporated, usually at levels up to 1.5%. The following patents disclose or refer to such ingredients and formulations which can be used in the soap/synbars of this invention, and are incorporated herein by reference:

| U.S. Pat. No. | Issue Date | Inventor(s) |
|---|---|---|
| 4,234,464 | 11/1980 | Morshauser |
| 4,061,602 | 12/1977 | Oberstar et al. |
| 4,472,297 | 9/1984 | Bolich et al. |
| 4,491,539 | 1/1985 | Hoskins et al. |
| 4,540,507 | 9/1985 | Grollier |
| 4,673,525 | 6/1987 | Small et al. |
| 4,704,224 | 11/1987 | Saud |
| 4,812,253 | 3/1989 | Small et al. |
| 4,820,447 | 4/1989 | Medcalf et al. |

EXAMPLES

The following examples are illustrative and are not intended to limit the scope of the invention(s). The detailed methods of making milled bars is well known. All levels and ranges, temperatures, results etc., used herein are approximations unless otherwise specified.

TABLE 1

| | Example Formulas (Wt. %) | |
|---|---|---|
| Ingredient | Ex. 1 | Ex. 2 |
| Sodium Tallowate | 22.66 | 37.34 |
| Sodium Palmate | 22.66 | — |
| Sodium Cocoate | 30.21 | 37.34 |
| Tallow Alkyl Polyethoxylate 80 | 3.30 | 5.00 |
| Sodium Coconut Acyl Isethionate | — | — |
| Coconut Fatty Acid | 4.80 | 5.35 |
| Glycerin | 3.00 | 3.00 |
| Guar Hydroxypropyl Trimonium Chloride | 0.92 | 1.00 |
| Polyquaternium-7 | — | — |
| Salt (Sodium Chloride/ Sodium Sulfate) | 1.10 | 1.10 |
| Fragrance | 1.00 | 1.50 |
| Titanium Dioxide | 0.30 | 0.32 |
| Preservative | 0.05 | 0.05 |
| Water | 10.00 | 8.00 |

COMPARATIVE TABLE 2

| Ingredient | Example Formulas (Wt. %) Ex. 3 | Ex. 4 |
|---|---|---|
| Sodium Tallowate | 37.34 | 37.34 |
| Sodium Palmate | — | — |
| Sodium Cocoate | 37.34 | 37.34 |
| Tallow Alkyl Polyethoxylate 50 | 5.00 | 3.00 |
| Sodium Coconut Acyl Isethionate | — | 2.00 |
| Coconut Fatty Acid | 5.35 | 5.35 |
| Glycerin | 3.00 | 3.00 |
| Guar Hydroxypropyl Trimonium Chloride | 1.00 | 1.00 |
| Salt (Sodium Chloride/ Sodium Sulfate) | 1.10 | 1.10 |
| Fragrance | 1.50 | 1.50 |
| Titanium Dioxide | 0.32 | 0.32 |
| Preservative | 0.05 | 0.05 |
| Water | 8.00 | 8.00 |

Comparative Examples 3 and 4 containing Tallow Alkyl Polyethoxylate 50 show frosting, crystallization of the nonionic surfactant, on the bar's surface while in storage. Examples 1 and 2 with high ethoxylated nonionic surfactant, Tallow Alkyl Polyethoxylate 80, show no surface crystallization under the same storage conditions, 46 days at 50° F. (10° C.).

What is claimed is:

1. A milled soap-synthetic bar comprising:

(1) from about 55% to about 80% soap;

(2) from about 0.5% to about 5% of cationic polymeric skin mildness aid selected from the group consisting of: (a) cationic polyalkylene imines, (b) cationic ethoxy polyalkylene imines, and (c) cationic poly[N-{-3-dimethylammonia)propyl}-N'-{3-(ethyleneoxyethylene dimethylammonio)propyl-}urea dichloride];

(3) from about 2% to about 5% of $C_{14-20}$ alkyl polyethoxylate nonionic detrgent surfactant containing from about 70 to about 100 ethylene oxide moieties per molecule; and (4) from about 8% to about 10% water; wherein the soap bar does not contain soap in the beta-phase form; and wherein the surface of the soap bar does not show frosting or crystallization of the nonionic surfactant after storage of the bar.

2. The bar of claim 1 wherein said cationic polymeric skin mildness aid (2) is present at a level of from about 0.5% to about 2%; said alkyl polyethoxylate (3) contains an alkyl group containing from about 16 to about 18 carbon atoms and from about 70 to about 90 ethylene oxide moieties per molecule.

3. The bar of claim 2 wherein said alkyl polyethoxylate (3) has an HLB of from about 15 to about 19.2.

4. The bar of claim 3 wherein said alkyl polyethoxylate (3)has an HLB of from about 17 to about 19.

5. The bar of claim 4 wherein said alkyl is a straight chain alkyl.

6. The bar of claim 3 wherein said alkyl is a straight chain alkyl.

7. The bar of claim 2, additionally comprising moisturizer selected from the group consisting of glycerin and fatty acids and the level of said moisturizer is from about 7% to about 12%.

8. The bar of claim 7 wherein said moisturizer comprises from about 4% to about 8% of said fatty acid and from about 2% to about 6% of said glycerin.

9. The bar of claim 1 wherein said alkyl polyethoxylate (3) has an HLB of from bout 15 to about 19.2.

10. The bar of claim 9 wherein said alkyl polyethoxylate (3) has an HLB of from about 17 to about 19.

11. The bar of claim 10 wherein said alkyl is a straight chain alkyl.

12. The bar of claim 9 wherein said alkyl is a straight chain alkyl.

13. The bar of claim 1, additionally comprising moisturizer selected from the group consisting of glycerin and fatty acids and the level of said moisturizer is from about 7% to about 12%.

14. The bar of claim 13 wherein said moisturizer comprises from about 4% to about 8% of said fatty acid and from about 2% to about of said glycerin.

15. The bar of claim 13 wherein said fatty acids are derived from tallow, coconut oil, palm kernel oil, palm oil stearin, or mixtures thereof.

16. The bar of claim 15 wherein said soap is derived from fatty acids are derived from tallow, coconut oil, palm kernel oil, palm oil stearin, or mixtures thereof.

* * * * *